United States Patent [19]

Gatechair et al.

[11] Patent Number: 5,258,138

[45] Date of Patent: Nov. 2, 1993

[54] PROCESS FOR STABILIZING ETHYLENICALLY UNSATURATED COMPOUNDS AND STABILIZED MONOMER COMPOSITIONS

[75] Inventors: Leslie R. Gatechair, Katonah; Raymond Seltzer, New City, both of N.Y.; James L. Hyun, Danbury, Conn.

[73] Assignee: Ciba-Geigy Corporation, Ardsley, N.Y.

[21] Appl. No.: 956,436

[22] Filed: Oct. 2, 1992

Related U.S. Application Data

[63] Continuation of Ser. No. 809,217, Dec. 16, 1991, abandoned, which is a continuation of Ser. No. 556,066, Jul. 20, 1990, abandoned.

[51] Int. Cl.$^5$ .............. C09K 15/22; C09K 15/16; C07C 69/52; C07C 61/16
[52] U.S. Cl. ................. 252/403; 252/405; 544/35; 544/38; 546/15; 546/22; 546/188; 546/189; 546/216; 546/226; 546/242; 546/245; 546/247; 546/248; 560/183; 560/201; 560/205; 562/510
[58] Field of Search .............. 544/35, 38; 546/15, 546/22, 188, 189, 216, 226, 242, 245, 247, 248; 252/403, 405; 560/183, 201, 205; 562/510

[56] References Cited

U.S. PATENT DOCUMENTS

| | | | |
|---|---|---|---|
| 3,014,888 | 12/1961 | Shimmin et al. | 544/38 |
| 3,148,225 | 9/1964 | Albert | 585/4 |
| 3,222,334 | 12/1965 | Demme | 526/83 |
| 3,408,422 | 10/1968 | May | 526/220 |
| 3,697,470 | 10/1972 | Haines et al. | 524/236 |
| 3,878,181 | 4/1975 | Mayer-Mader et al. | |
| 4,409,408 | 10/1983 | Miller | 585/4 |
| 4,434,307 | 2/1984 | Miller | 585/4 |
| 4,670,131 | 2/1987 | Ferrell | 208/48 |
| 4,691,015 | 9/1987 | Behrens et al. | 546/188 |
| 4,782,105 | 11/1988 | Ravichandran et al. | 524/236 |
| 4,798,889 | 1/1989 | Plueddemann et al. | 556/401 |
| 4,912,247 | 3/1990 | Roling | 558/306 |
| 4,915,873 | 4/1990 | Abruscatel et al. | 252/402 |
| 5,130,471 | 7/1992 | Heiman et al. | 560/205 |

FOREIGN PATENT DOCUMENTS

| | | |
|---|---|---|
| 0178168 | 4/1986 | European Pat. Off. |
| 60-36501 | 2/1985 | Japan |
| 1139722 | 2/1985 | U.S.S.R. |
| 1127127 | 10/1968 | United Kingdom |

OTHER PUBLICATIONS

Y. Miura et al., Makromol. Chem. 160,243 (1972).
Derwent Abst. 89-279844/39, 1989.

Primary Examiner—Mukund J. Shah
Assistant Examiner—Y. N. Gupta
Attorney, Agent, or Firm—Luther A. R. Hall

[57] ABSTRACT

A process for stabilizing an ethylenically unsaturated monomer or oligomer from premature polymerization is disclosed whereby a stabilizing amount of an amine, preferably a substituted hindered amine, in combination with phenothiazine or other related heterocyclic moiety is added to said polymerizable monomer or oligomer. The ethylenically unsaturated monomer or oligomer encompass vinyl monomers or oligomers bearing at least one polymerizable moiety. The combination of substituted hindered amine plus phenothiazine inhibits premature polymerization in the liquid and/or vapor phase.

4 Claims, No Drawings

PROCESS FOR STABILIZING ETHYLENICALLY UNSATURATED COMPOUNDS AND STABILIZED MONOMER COMPOSITIONS

This is a continuation of application Ser. No. 809,217, filed on Dec. 16, 1991, now abandoned, which is a continuation of application Ser. No. 556,066, filed on Jul. 20, 1990, now abandoned.

The instant invention pertains to a process for stabilizing an ethylenically unsaturated monomer or oligomer from premature polymerization in the liquid and/or vapor phase by adding thereto a stabilizing amount of an amine, preferably a substituted hindered amine, plus phenothiazine or other related heterocyclic moiety.

BACKGROUND OF THE INVENTION

The ethylenically unsaturated compounds which can be polymerized by free radical initiation are commonly called monomers. They constitute a major class of industrial chemicals. Because of the presence of the polymerizable double bond, the widespread sources of initiating radicals from peroxides, light and/or thermal generation, such monomers are prone to undesirable and premature polymerization at various stages during their manufacture, purification, storage, shipping, blending and use. Protection of such monomers from such premature polymerization is needed up to the point where polymerization is actually desired. If premature polymerization does occur, the monomer may suffer contamination by polymer, troublesome increase in viscosity, gelation and/or loss of reactivity. Fouling of distillation equipment including heat exchanger surfaces, storage vessels, transfer lines, pumps, shipping containers and application equipment can occur with ensuing costs of cleaning, downtime, loss of material and unnecessary labor costs. A particularly difficult situation is the preparation of polyol acrylates from polyols and acrylic acid since prolonged heating periods are required to complete the esterification. Premature polymerization can also constitute a safety hazard since uncontrolled exothermic polymerization can cause ruptured vessels, atmospheric contamination, and in extreme cases, explosions and fires. Deterioration of monomers in shipping and storage may also make necessary the use of costly refrigerated shipping and storage facilities.

A further problem is that of undesired polymerization of adventitious monomers, that is, radically-polymerizable unsaturated monomers which occur in commercial products such as hydrocarbon fuels and refinery streams. In these cases, polymerization accompanied by the incorporation of oxygen moieties leads to gum and sludge deposits which can foul carburetors, engines, fuel tanks or fuel lines. In refineries, the adventitious monomers in hydrocarbon streams such as cracking products can foul pipelines, valves, pumps, heat exchangers, stills and storage vessels.

Another problem in regard to undesired polymerization of free radical polymerizable monomers is the case of polymerizations which are intentional, but which must be prevented from going too far. For example, the quality of poly(vinyl chloride) suspension polymer and of synthetic rubber made from olefins and dienes is superior (i.e. better molecular weight distribution, stability, and processing properties) if the polymerization is stopped short of complete consumption of the monomers. It is also desirable to have available in a plant conducting vinyl polymerization reactions some rapid and efficient means for stopping a runaway polymerization if other means such as cooling should fail.

It is known that the addition of certain compounds to monomers can retard or even prevent their undesired polymerization, and that when polymerization of the monomer is desired, the inhibitor can be removed or overridden by a deliberately-added polymerization initiator. Various aromatic compounds have been used as such inhibitors in the prior art. Typical ones are hydroquinone, monomethyl ether of hydroquinone (MEHQ), tert-butylphenols, phenothiazine, phenylenediamines and benzoquinones. These are usually used at a level of 50 to 1000 ppm. These inhibitors are not totally effective, and even with such inhibitors present, it is often advisable to store such inhibited monomers in a cool place and for limited periods of time. Moreover, these aromatic inhibitors are a cause of serious discoloration problems in the monomers and in polymers deliberately prepared from such monomers. Typically these aromatic inhibitors produce quinoidal chromophoric groups with very high visible light absorbance. The use of stable nitroxyl radicals as inhibitors also leads to discoloration since such compounds are themselves highly colored, usually bright red.

In order to overcome these color problems, a diligent search was made to find alternative inhibitors which are both effective and not discoloring. This search led to the N,N-dialkylhydroxylamines and the N,N-diaralkylhydroxylamines. Some typical references are cited infra.

U.S. Pat. Nos. 3,222,334 and 3,878,181 disclose the use of N,N-dialkylhydroxylamines such as N,N-diethylhydroxylamine as short-stopping agents for emulsion polymerizations of butadiene/styrene rubber and chloroprene.

U.S. Pat. Nos. 3,148,225 and 3,697,470 disclose the use of N,N-dialkylhydroxylamines such as N,N-diethylhydroxylamine and N-alkyl-N-arylhydroxylamine such as N-ethyl-N-phenylhydroxylamine respectively as short-stopping agents and popcorn polymer inhibitors in processes for preparing synthetic rubber. The popcorn polymer formation is a serious problem encountered in recovering of monomers from such synthetic rubber operations.

U.S. Pat. No. 4,782,105 teaches the use of long chain N,N-dialkylhydroxylamines as stabilizers to prevent the premature gelation of unsaturated elastomer compositions such as styrene/butadiene copolymers or polybutadiene.

U.S. Pat. No. 3,408,422 describes the use of N,N-dialkylhydroxylamines such as N,N-diethylhydroxylamine and N,N-diaralkylhydroxylamines such as N,N-dibenzylhydroxylamine as stabilizers for preventing the premature gelation of unsaturated polyesters.

U.S. Pat. No. 4,798,889 teaches the use of N,N-dialkylhydroxylamines such as N,N-diethylhydroxylamine or N,N-dibenzylhydroxylamine as stabilizer to reduce the thermal polymerization of organosiloxanes substituted by-ethylenically unsaturated moieties.

U.S. Pat. Nos. 4,409,408 and 4,434,307 disclose the use of N,N-dibenzylhydroxylamine in combination with an alkylated diphenol (catechol or hydroquinone) as inhibitors to prevent the polymerization of styrene.

The use of stable nitroxyl radicals including those derived from hindered amine moieties has also been disclosed. Typical references are cited below.

Russian Published Application No. 1,139,722 describes the inhibition of styrene and comonomers such as butadiene using 1-oxyl derivatives of hindered amine compounds such as N,N'-bis(1-oxyl-2,2,6,6-tetramethylpiperidin-4-yl)adipamide. The elimination of popcorn polymer and of the clogging of equipment is touted as the result of using such 1-oxyl compounds.

Japanese Sho 60-36501 describes the use of hindered amines and their 1-oxyl and 1-alkyl derivatives as vinyl polymerization inhibitors to improve storage stability of monomers such as acrylate and methacrylate esters.

European Patent Application No. 178,168 and British Patent No. 1,127,127 describe the use of 1-oxyl substituted hindered amine compounds as stabilizers for inhibiting the polymerization of $\alpha,\beta$-ethylenically unsaturated monocarboxylic acids, such as acrylic acid, during its recovery by distillation.

U.S. Pat. No. 4,670,131 teaches the use of 1-oxyl substituted hindered amine compounds as stabilizers for preventing the fouling of equipment for processing organic feed streams containing olefins by inhibiting the polymerization of said olefins.

In a theretical study of the inhibiting effects of selected hindered amine compounds, Y. Miura et al., Makromol. Chem. 160, 243 (1972) disclose that 1-oxyl-2,2,6,6-tetramethylpiperidin-4-one is highly effective in retarding the onset of the polymerization of styrene and methyl methacrylate. By contrast, the corresponding 1-benzyloxy-2,2,6,6-tetramethylpiperidin-4-one is stated to have no effect in delaying the polymerization of styrene and no retarding effect on said polymerization once begun.

U.S. Pat. Nos. 4,668,721 and 4,691,015 disclose the use of 1-hydroxy substituted hindered amine compounds as stabilizers for polyolefin compositions in combination with one or more other stabilizers such as phenolic antioxidants, ultraviolet light absorbers and the like.

Copending U.S. patent application Ser. No. 259,950 describes N-hydrocarbyloxy substituted hindered amine compounds as useful light stabilizers for a variety of substrates.

European Patent application No. 334,500 (Derwent 89-279844/39) describes polymerization inhibition compositions comprising (a) a phenothiazine and (b) a substituted phenylenediamine for inhibiting the polymerization of styrene.

None of these references describes or suggests that a substituted hindered amine plus phenothiazine or other related heterocyclic moiety is or could possibly be such effective inhibitors to prevent the premature polymerization of monomers in either the liquid or vapor phase.

OBJECTS OF THE INVENTION

It is the broad object of the invention to provide monomer compositions inhibited against undesired and premature polymerization by means of small, but effective amounts of selected additives which do not impart undesired color to the monomer compositions.

It is a further object of the invention to provide inhibited monomer compositions which have substantially improved stability relative to compositions inhibited by methods known in the prior art.

It is a further object of the invention to provide a means for short-stopping or retarding polymerization of monomers once polymerization is started.

It is a further object of the invention to provide effective inhibitors for monomers known to be difficult to inhibit such as acrylic acid.

It is still a further object of the invention to provide highly effective combinations of inhibitors for said monomers.

DETAILED DISCLOSURE

The invention pertains to a monomer composition, stabilized against premature polymerization, which comprises (a) an ethylenically unsaturated monomer or mixture of monomers, polymerizable by free radical initiation, and (b) an effective amount, sufficient to inhibit the premature polymerization of component (a), which is a combination of (i) a heterocyclic compound selected from any of formulas A to C

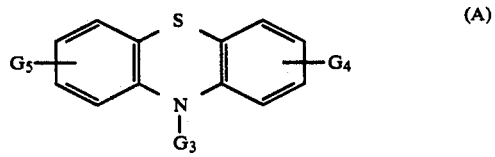

(A)

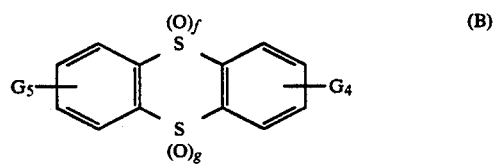

(B)

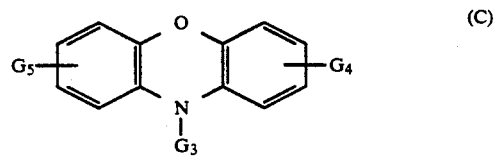

(C)

where $G_3$ is hydrogen, alkyl of 1 to 4 carbon atoms or alkenyl of 3 to 4 carbon atoms, preferably hydrogen, allyl or 1-propenyl, most preferably hydrogen, $G_4$ and $G_5$ are independently hydrogen or alkyl of 1 to 8 carbon atoms, preferably hydrogen, and f and g are independently 0, 1 or 2, and (ii) a primary, secondary or tertiary amine, or hydroxylamine, or mixture thereof, of the formula

$NQ_2Q_3Q_4$

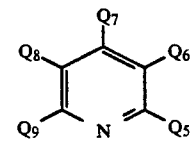

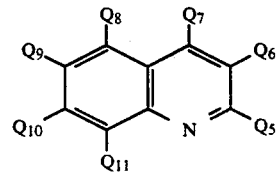

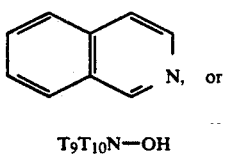

wherein

Q₂, Q₃ and Q₄ are independently hydrogen, alkyl of 1 to 18 carbon atoms, said alkyl substituted by hydroxy, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by alkyl of 1 to 12 carbon atoms or by phenyl, with the proviso that all of $Q_2$, $Q_3$ and $Q_4$ are not hydrogen, cycloalkyl, phenylalkyl or aryl at the same time; or $Q_3$ and $Q_4$ together are straight or branched alkylene of 4 to 8 carbon atoms, 3-oxapentamethylene, 3-thiapentamethylene, 3-iminopentamethylene or 3-methyliminopentamethylene, and $Q_2$ is hydrogen or alkyl of 1 to 8 carbon atoms;

$Q_5$, $Q_6$, $Q_7$, $Q_8$, $Q_9$, $Q_{10}$ and $Q_{11}$ are independently hydrogen, methyl or ethyl, preferably hydrogen or methyl, most preferably hydrogen; or $T_9$ is hydrogen, alkyl of 1 to 18 carbon atoms, cycloalkyl of 5 to 12 carbon atoms or phenylalkyl of 7 to 15 carbon atoms, and $T_{10}$ is alkyl of 1 to 18 carbon atoms, cycloalkyl of 5 to 12 carbon atoms or phenylalkyl of 7 to 15 carbon atoms.

Preferably component (ii) is a compound or mixture of compounds of any of formulas I to XIX

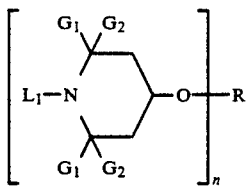 (I)

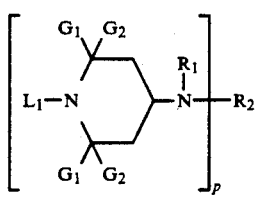 (II)

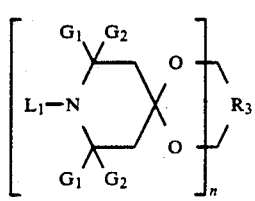 (III)

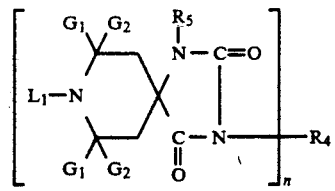 (IV)

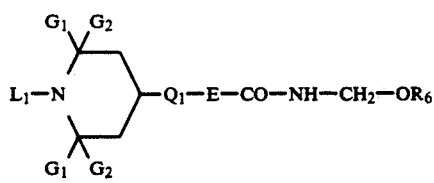 (V)

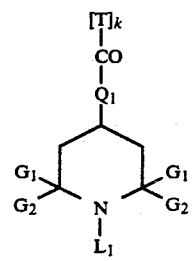 (VI)

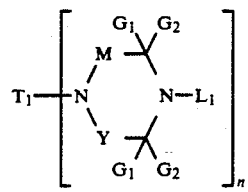 (VII)

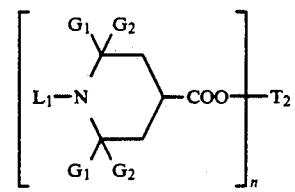 (VIII)

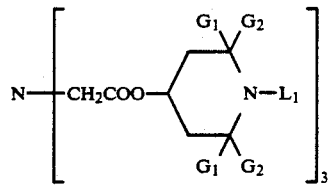 (IX)

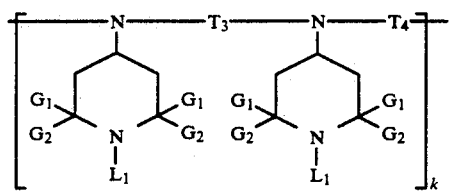 (X)

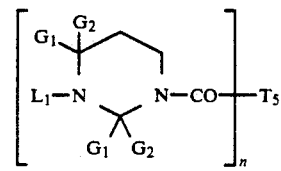 (XI)

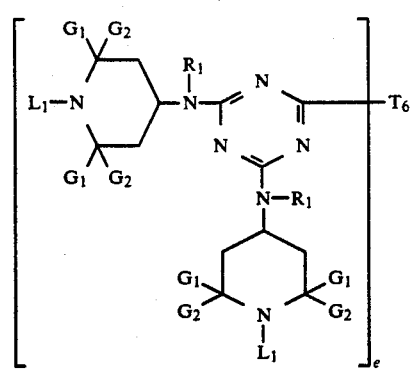
(XII)

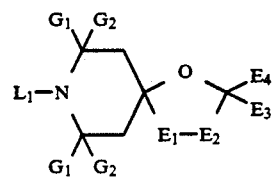
(XIII)

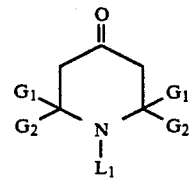
(XIV)

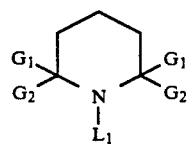
(XV)

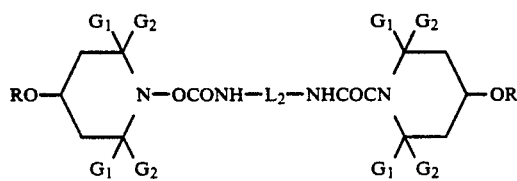
XVI

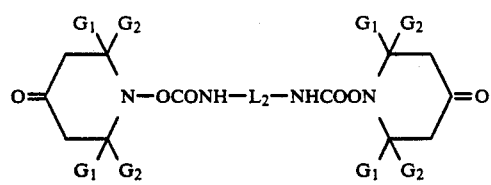
XVII

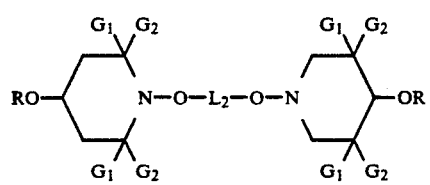
XVIII

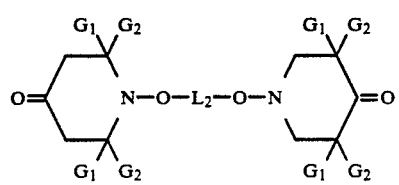
XIX wherein $G_1$ and $G_2$ are independently alkyl of 1 to 4 carbon atoms, preferably methyl, or $G_1$ and $G_2$ together are pentamethylene;

$L_1$ is hydrogen, hydroxyl, alkyl of 1 to 18 carbon atoms, said alkyl substituted by hydroxyl, cyanoethyl, glycidyl, aralkyl of 7 to 15 carbon atoms or a monovalent acyl radical of an aliphatic, cycloaliphatic, araliphatic or aromatic acid, —OCONHL$_3$ or —OL$_4$, where $L_3$ is hydrogen, alkyl of 2 to 18 carbon atoms, allyl, cyclohexyl, aryl of 6 to 10 carbon atoms, said aryl substituted by one or two alkyl groups of 1 to 4 carbon atoms or is benzyl, $L_4$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl of 1 to 4 carbon atoms, or $L_4$ is —CH$_2$CH$_2$COOL$_5$ where $L_5$ is alkyl of 1 to 18 carbon atoms, n is 1 or 2, when n is 1, R is hydrogen, $C_1$-$C_{18}$-alkyl optionally interrupted by one or more oxygen atoms, cyanoethyl, benzyl, glycidyl, a monovalent acyl radical of an aliphatic, cycloaliphatic, araliphatic or aromatic acid, or of carbamic acid or of a phosphorus-containing acid, or a monovalent silyl radical, preferably an acyl radical of an aliphatic carboxylic acid having 2 to 18 carbon atoms, of a cycloaliphatic acid having 5 to 12 carbon atoms or of an aromatic carboxylic acid having 7 to 15 carbon atoms, or of carbamic acid; or when n is 2, R is $C_1$-$C_{12}$-alkylene, $C_4$-$C_{12}$-alkenylene, xylylene, a divalent acyl radical of an aliphatic, cycloaliphatic, araliphatic or aromatic dicarboxylic acid, or of a dicarbamic acid or of a phosphorus-containing acid, or a bivalent silyl radical, preferably an acyl radical of an aliphatic dicarboxylic acid having 2 to 36 carbon atoms, of a cycloaliphatic or aromatic dicarboxylic acid having 8 to 14 carbon atoms, or of a aromatic dicarbamic acid having 8 to 14 carbon atoms;

p is 1, 2 or 3, $R_1$ is $C_1$-$C_{12}$-alkyl, $C_5$-$C_7$-cycloalkyl, $C_7$-$C_8$-aralkyl, $C_2$-$C_{18}$-alkanoyl, $C_3$-$C_5$-alkenoyl or benzoyl;

when p is 1, $R_2$ is $C_1$-$C_{18}$-alkyl, $C_5$-$C_7$-cycloalkyl, $C_2$-$C_8$-alkenyl unsubstituted or substituted by a cyano, carbonyl or carbamide group, or is glycidyl, a group of the formula —CH$_2$CH(OH)—Z or of the formula —CONH—Z wherein Z is hydrogen, methyl or phenyl; or when p is 2, $R_2$ is $C_2$-$C_{12}$-alkylene, $C_6$-$C_{12}$-arylene, xylylene, a —CH$_2$CH(OH)CH$_2$—O—X—O—CH$_2$CH(OH)CH$_2$—wherein X is $C_2$-$C_{10}$-alkylene, $C_6$-$C_{15}$-arylene or $C_6$-$C_{12}$-cycloalkylene; or, provided that $R_1$ is not alkanoyl, alkenoyl or benzoyl, $R_2$ can also be a divalent acyl radical of an aliphatic, cycloaliphatic or aromatic dicarboxylic acid or dicarbamic acid, or can be the group —CO—; or $R_1$ and $R_2$ together when p is 1 can be the cyclic acyl radical of an aliphatic or aromatic 1,2- or 1,3-dicarboxylic acid; or $R_2$ is $$\begin{array}{c} \phantom{X} \\ N \diagup \diagdown N \\ | \phantom{XX} | \\ N \diagdown \diagup N \\ | \\ N \\ \diagup \diagdown \\ T_7 \phantom{XX} T_8 \end{array}$$

where $T_7$ and $T_8$ are independently hydrogen, alkyl of 1 to 18 carbon atoms, or $T_7$ and $T_8$ together are alkylene of 4 to 6 carbon atoms or 3-oxapentamethylene, preferably $T_7$ and $T_8$ are 3-oxapentamethylene;

when p is 3,
$R_2$ is 2,4,6-triazinyl;
when n is 1,
$R_3$ is $C_2$-$C_8$-alkylene or hydroxyalkylene or $C_4$-$C_{22}$-acyloxyalkylene; or
when n is 2,
$R_3$ is $(-CH_2)_2C(CH_2-)_2$;
when n is 1,
$R_4$ is hydrogen, $C_1$-$C_{12}$-alkyl, $C_3$-$C_5$-alkenyl, $C_7$-$C_9$-aralkyl, $C_5$-$C_7$-cycloalkyl, $C_2$-$C_4$-hydroxyalkyl, $C_2$-$C_6$-alkoxyalkyl, $C_6$-$C_{10}$-aryl, glycidyl, a group of formula $-(CH_2)_m-COO-Q$ or of the formula $-(CH_2)_m-O-CO-Q$ wherein m is 1 or 2 and Q is $C_1$-$C_4$-alkyl or phenyl; or
when n is 2,
$R_4$ is $C_2$-$C_{12}$-alkylene, $C_6$-$C_{12}$-arylene, a group $-CH_2CH(OH)CH_2-O-X-O-CH_2CH(OH)CH_2-$ wherein X is $C_2$-$C_{10}$-alkylene, $C_6$-$C_{15}$-arylene or $C_6$-$C_{12}$-cycloalkylene, or a group $-CH_2CH(OZ_1)CH_2-(OCH_2CH(OZ_1)CH_2)_2-$ wherein $Z_1$ is hydrogen, $C_1$-$C_{18}$-alkyl, allyl, benzyl, $C_2$-$C_{12}$-alkanoyl or benzoyl;
$R_5$ is hydrogen, $C_1$-$C_{12}$-alkyl, allyl, benzyl, glycidyl or $C_2$-$C_6$-alkoxyalkyl;
$Q_1$ is $-N(R_7)-$ or $-O-$;
E is $C_1$-$C_3$-alkylene, the group $-CH_2CH(R_8)-O-$ wherein $R_8$ is hydrogen, methyl or phenyl, the group $-(CH_2)_3-NH-$ or a direct bond;
$R_7$ is $C_1$-$C_{18}$-alkyl, $C_5$-$C_7$-cycloalkyl, $C_7$-$C_{12}$-aralkyl, cyanoethyl, $C_6$-$C_{10}$-aryl, the group $-CH_2CH(R_8)-OH$; or a group of the formula $$\begin{array}{c} G_1 \phantom{XX} G_2 \\ \diagdown \phantom{X} \diagup \\ L_1-N \\ \diagup \phantom{X} \diagdown \\ G_1 \phantom{XX} G_2 \end{array}$$

or a group of the formula $$-G-N-E-CO-NH-CH_2-OR$$
$$\begin{array}{c} G_1 \phantom{XXXX} G_1 \\ G_2 \diagdown \phantom{X} \diagup G_2 \\ N \\ | \\ L_1 \end{array}$$

wherein
G is $C_2$-$C_6$-alkylene or $C_6$-$C_{12}$-arylene; or $R_7$ is a group $-E-CO-NH-CH_2-OR_6$;
$R_6$ is hydrogen or $C_1$-$C_{18}$-alkyl;
Formula VI denotes a recurring structural unit of a polymer where T is ethylene or 1,2-propylene, or is a repeating structural unit derived from an α-olefin copolymer with an alkyl acrylate or methacrylate, preferably a copolymer of ethylene and ethyl acrylate;
k is 2 to 100;
$T_1$ has the same meaning as $R_2$ when p is 1 or 2;
M and Y are independently methylene or carbonyl, preferably M is methylene and Y is carbonyl, and $T_1$ is ethylene when n is 2;
$T_2$ has the same meaning as $R_4$, and $T_2$ is preferably octamethylene when n is 2,
$T_3$ and $T_4$ are independently alkylene of 2 to 12 carbon atoms, of $T_4$ is $$\begin{array}{c} \phantom{X} \\ N \diagup \diagdown N \\ | \phantom{XX} || \\ N \diagdown \diagup N \\ | \\ N \\ \diagup \diagdown \\ T_7 \phantom{XX} T_8 \end{array}$$

$T_6$ is $$-NH(CH_2)_a-\overset{|}{N}(CH_2)_b-\overset{|}{N}[(CH_2)_c-\overset{|}{N}-]_dH$$

where a, b and c are independently 2 or 3, and d is 0 or 1, preferably a and c are each 3, b is 2 and d is 1;
e is 3 or 4, preferably 4;
$T_5$ is the same as R with the proviso that $T_5$ cannot be hydrogen when n is 1;
$E_1$ and $E_2$, being different, are each oxo or imino, preferably $E_1$ is oxo and $E_2$ is $-N(E_5)-$ where $E_5$ is $C_1$-$C_{12}$-alkyl or alkoxycarbonylalkyl of 4 to 22 carbon atoms;
$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms;
$E_4$ is hydrogen, alkyl of 1 to 30 carbon atoms, phenyl, naphthyl or phenylalkyl of 7 to 12 carbon atoms; or
$E_3$ and $E_4$ together are polymethylene of 4 to 17 carbon atoms, or said polymethylene substituted by up to four alkyl groups of 1 to 4 carbon atoms, preferably methyl; and
$L_2$ is a divalent radical from an aliphatic, cycloaliphatic or aromatic diisocyanate from which the two $-NCO$ groups are removed, or is an alkanediyl of 1 to 18 carbon atoms or cyclohexanediyl;
wherein the weight ratio of component (i):component (ii) is from 1:10 to 1000:1, preferably 1:1 to 10:1 where the total concentration is in the range of 50–10,000 ppm (preferred 200–600 ppm) based on the monomer being stabilized.

Still another aspect of the instant invention pertains to a monomer composition, stabilized against premature polymerization, which comprises (a) an ethylenically unsaturated monomer or mixture of monomers, polymerizable by free radical initiation, and (b) an effective amount, sufficient to inhibit the premature polymerization of component (a), which is a combination of (i) a phenylenediamine compound of formula D

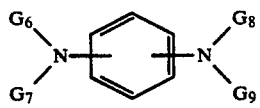

where $G_6$ is aryl of 6 to 10 carbon atoms or aralkyl of 7 to 15 carbon atoms, and $G_7$, $G_8$ and $G_9$ are independently hydrogen, alkyl of 1 to 18 carbon atoms, cycloalkyl of 5 to 12 carbon atoms, aralkyl of 7 to 15 carbon atoms or alkaryl of 7 to 15 carbon atoms; and (ii) a compound or mixture of compounds of formula I to XIX, as described above.

The monomers of component (a) of this invention are any having at least one carbon-carbon double bond capable of undergoing free radical induced polymerization. Such monomers are well known in commerce and comprise a wide variety of structural types. Typical examples of such monomers are the olefinic hydrocarbons such as styrene, α-methylstyrene and divinylbenzene; dienes such as butadiene and isoprene; halogenated monomers such as vinyl chloride, chloroprene, vinylidene chloride, vinylidene fluoride and vinyl fluoride; unsaturated acids such as acrylic acid, methacrylic acid and crotonic acid; unsaturated esters such as vinyl acetate, alkyl acrylates and alkyl methacrylates such as methyl methacrylate, ethyl acrylate, methyl acrylate, 2-hydroxyethyl acrylate and methacrylate, ethylene bismethacrylate, trimethylolpropane triacrylate, acrylated epoxy resin and polyethylene glycol diacrylate; unsaturated amides such as acrylamide, N,N-dimethylacrylamide, methylene-bisacrylamide and N-vinylpyrrolidone; unsaturated nitrile monomers such as acrylonitrile; and unsaturated ethers such as methyl vinyl ether; and miscellaneous monomers such as the vinyl pyridines, diethyl vinylphosphonate and sodium styrenesulfonate.

The instant invention also pertains to mixtures of said monomers and to resins such as acrylate-terminated polyurethanes and unsaturated polyesters. The common feature making all of these materials relevant to the present invention is the presence of a polymerizable double bond.

Also in the category of monomers are unsaturated oils such as drying oils like linseed oil, where polymerization also incorporates oxygen. There are also adventitious monomers formed in refining processes, for example polymerizable olefinic unsaturation in gasoline, jet fuel, solvents, crude oil and cracked hydrocarbon streams. The common feature of all of these substances is encompassed in the broad term "monomers" and all are contemplated to be within the scope of instant component (a). Polymerization of such materials is often accompanied by autooxidation.

The acrylates, particularly acrylic acid itself, are unusually difficult to inhibit because of their inherent high polymerizability. The instant compounds are shown to be particularly effective in inhibiting acrylic acid from premature polymerization.

Preferably component (a) is a monomer selected from the group consisting of the olefinic hydrocarbons, dienes, halogenated monomers, unsaturated acids, unsaturated esters, unsaturated amides, unsaturated nitriles, unsaturated ethers, acrylated urethanes and unsaturated polyesters and mixtures thereof.

Most preferably the monomer of component (a) is styrene, butadiene, vinyl chloride, acrylic acid, methacrylic acid, vinyl acetate, 2-hydroxyethyl acrylate, 2-hydroxyethyl methacrylate, trimethylolpropane triacrylate, polyethylene glycol diacrylate or methyl methacrylate.

Still more preferably the monomer is styrene, butadiene, acrylic acid or methacrylic acid.

The N-hydrocarbyloxy derivatives useful in the instant invention are denoted by the various structures of formulas I to XV. Most of these N-hydrocarbyloxy derivatives are known compounds. The instant N-hydrocarbyloxy derivatives can be easily prepared from the corresponding hindered amines which are known or which can be made by known procedures.

The hydroxylamine derivative may generally be prepared by oxidizing a hindered amine with a peroxy compound such as hydrogen peroxide followed by reduction of the oxyl intermediate formed to the desired hydroxylamine derivative. Such a process is taught in U.S. Pat. No. 4,665,185.

The instant N-hydrocarbyloxy derivatives are made by reacting a hydroxylamine with an alkyl halide or benzyl halide or reacting the hydroxylamine with an alkyl in presence of potassium butoxide.

Another method involves the preparation of the N-hydrocarbyloxy compounds directly from the hindered amine precursors using aqueous tert-butyl hydroperoxide, molybdenum trioxide in an appropriate hydrocarbon medium.

If any of the substituents are $C_1-C_{12}$-alkyl, they are for example methyl, ethyl, n-propyl, isopropyl, n-butyl, sec-butyl, tert-butyl, n-amyl, tert-amyl, n-hexyl, n-octyl, 2-ethylhexyl, tert-octyl, n-nonyl, n-decyl, n-undecyl or n-dodecyl. As $C_1-C_{18}$-alkyl, R can be the aforementioned groups, and in addition for example n-tridecyl, n-tetradecyl, n-hexadecyl or n-octadecyl.

$L_1$ is particularly hydrogen, hydroxyl, alkyl of 1 to 12 carbon atoms, $-OCONHL_3$ where $L_3$ is hydrogen, alkyl of 2 to 8 carbon atoms or phenyl, or $-OL_4$ where $L_4$ is particularly alkyl of 1 to 12 carbon atoms, cycloalkyl of 5 to 8 carbon atoms or is $-CH_2CH_2COOL_5$ where $L_5$ is particularly alkyl of 1 to 12 carbon atoms.

If R is a monovalent acyl radical of a carboxylic acid, it is for example an acyl radical of acetic acid, stearic acid, salicylic acid, methacrylic acid, acrylic acid, maleic acid, benzoic acid, 2-ethylhexanoic acid or 3,5-di-tert-butyl-4-hydroxyhydrocinnamic acid.

If R is a divalent acyl radical of a dicarboxylic acid, it is for example an acyl radical of adipic acid, succinic acid, suberic acid, sebacic acid, o-phthalic acid, butylmalonic acid, dibutylmalonic acid, dibenzylmalonic acid, 3,5-di-tert-butyl-4-hydroxybenzyl-butylmalonic acid or bicycloheptene dicarboxylic acid.

If R is a divalent acyl radical of a dicarbamic acid, it is for example an acyl radical of hexamethylenedicarbamic acid or 2,4-toluylenedicarbamic acid.

R is also an acyl radical of a phosphorus-containing acid of the formula

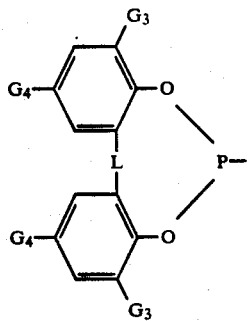

wherein

L is a direct bond, methylene or alkylidene of 2 to 6 carbon atoms such as ethylidene, butylidene or amylidene. Preferably L is a direct bond, methylene or ethylidene.

$G_3$ and $G_4$ are independently alkyl of 1 to 4 carbon atoms, preferably methyl or tert-butyl. Most preferably $G_3$ and $G_4$ are each tert-butyl, or $G_3$ is tert-butyl and $G_4$ is methyl.

If any substituents are $C_5$-$C_7$-cycloalkyl, they are in particular cyclohexyl.

As $C_7$-$C_8$-aralkyl, $R_1$ is phenethyl and especially benzyl.

As $C_2$-$C_{18}$-alkanoyl, $R_1$ is for example propionyl, butyryl, octanoyl, lauroyl, hexadecanoyl, octadecanoyl, but especially acetyl; and as $C_3$-$C_5$-alkenoyl, $R_1$ is in particular acryloyl.

If $R_2$ is $C_2$-$C_8$-alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

When $R_1$ and $R_2$ are together a cyclic acyl radical, they are especially —CO—$(CH_2)_5$—.

If any substituents are $C_2$-$C_{12}$-alkylene, they are for example ethylene, propylene, 2,2-dimethylpropylene, tetramethylene, hexamethylene, octamethylene, decamethylene or dodecamethylene.

If any substituents are $C_6$-$C_{15}$-arylene, they are for example o-, m- or p-phenylene, 1,4-naphthylene or 4,4'-diphenylene.

As $C_6$-$C_{12}$-cycloalkylene, X is especially cyclohexylene.

If $R_3$ is $C_2$-$C_8$-alkylene or hydroxyalkylene, it is for example ethylene, 1-methyl-ethylene, propylene, 2-ethylpropylene or 2-ethyl-2-hydroxymethylpropylene.

As $C_4$-$C_{22}$acyloxyalkylene, $R_3$ is for example 2-ethyl-2-acetoxymethyl-propylene.

If any substituents are $C_2$-$C_6$-alkoxyalkyl, they are example methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

If $R_4$ is $C_3$-$C_5$-alkenyl, it is for example 1-propenyl, allyl, methallyl, 2-butenyl or 2-pentenyl.

As $C_7$-$C_9$-aralkyl, $R_4$ is phenethyl or especially benzyl; and as $C_5$-$C_7$-cyclohexyl is especially cyclohexyl.

If $R_4$ is $C_2$-$C_4$-hydroxyalkyl, it is for example 2-hydroxyethyl, 2-hydroxypropyl, 3-hydroxypropyl, 2-hydroxybutyl or 4-hydroxybutyl.

As $C_6$-$C_{10}$-aryl, $R_4$ is in particular phenyl or α- or β-naphthyl which is unsubstituted or substituted by halogen or $C_1$-$C_4$-alkyl.

If $R_4$ is $C_2$-$C_{12}$-alkylene, it is for example ethylene, propylene, 2,2-dimethylpropylene, tetramethylene, hexamethylene, octamethylene, decamethylene or dodecamethylene.

If $R_4$ is $C_6$-$C_{12}$-arylene, it is for example o-, m- or p-phenylene, 1,4-naphthylene or 4,4'-diphenylene.

If $Z_1$ is $C_2$-$C_{12}$-alkanoyl, it is for example propionyl, butyryl, octanoyl, dodecanoyl or preferably acetyl.

As $C_5$-$C_7$-cycloalkyl, $R_7$ is particularly cyclohexyl.

As $C_6$-$C_{10}$-aryl, $R_7$ is particularly phenyl or α- or β-naphthyl which is unsubstituted or substituted with halogen or $C_1$-$C_4$-alkyl.

As $C_1$-$C_3$-alkylene, E is for example methylene, ethylene or propylene.

As $C_2$-$C_6$-alkylene, G is for example ethylene, propylene, 2,2-dimethylpropylene, tetramethylene or hexamethylene; and as $C_6$-$C_{12}$-arylene, G is o-, m- or p-phenylene, 1,4-naphthylene or 4,4'-diphenylene.

Diisocyanates of the formula $L_2$-$(NCO)_2$ useful to form the compounds of formula XVI or XVII are aliphatic, cycloaliphatic or aromatic diisocyanates and are selected from the group consisting of ethylene diisocyanate, 1,2-diisocyanatopropane, 1,3-diisocyanatopropane, 1,6-diisocyanatohexane, 1,2-diisocyanatocyclohexane, 1,3-diisocyanatocyclohexane, 1,4-diisocyanatobenzene, bis(4-isocyanatocyclohexyl)methane, bis(4-isocyanatocyclohexenyl)methane, bis(4-isocyanato-phenyl)methane, 2,6- and 2,4-toluene diisocyanate, 3,3-dichloro-4,4'-diisocyanatobiphenyl, 1,5-diisocyanatonaphthalene, hydrogenated toluene diisocyanate, 1-isocyanato-5-isocyanato-1,3,3-trimethylcyclohexane (=isophorone diisocyanate), 2,2'-diisocyanatodiethyl fumarate, 1,5-diisocyanato-1-carboxypentane, 1,2-, 1,3-, 1,6-, 1,7-, 2,7- and 2,3-diisocyanatonaphthalene, 2,4- and 2,7-diisocyanato-1-methylnaphthalene, 4,4'-diisocyanatobiphenyl, bis(4-isocyanatophenyl)ethane, bis(4-isocyanatophenyl) ether and 2,2,4-(2,4,4)-trimethylhexane-1,6-diisocyanate.

The preferred diisocyanates are isophorone diisocyanate, 2,2,4-(2,4,4)-trimethylhexane-1,6-diisocyanate and 2,4- and 2,6-toluene diisocyanate.

An effective inhibiting amount of an instant components (i) and (ii) of this invention needed to reatard or prevent premature free radical induced polymerization of a monomer or monomer mixture is as follows: the weight ratio of component (i) to component (ii) is from 1:10 to 1000:1, preferably 1:1 to 10:1, and where the total concentration is in the range of 50–10,000 ppm, preferably 200–600 ppm, based on the monomer being stabilized. The lower amounts would be used where the degree of inhibition required is not great such as when the monomers are to be used promptly, or which will be stored refrigerated, or which are inherently less prone to polymerize readily such as monomers with internal double bonds. The higher amounts of inhibitor would be used where the monomer is to be stored for prolonged periods of time, especially under relatively warm conditions or where contamination is likely, or where exposure to photoinitiation is likely, or where the monomer is especially prone to rapid polymerization with little provocation such as with the acrylates and acrylic acid. Those skilled in the art of vinyl polymerization are well aware of the relative polymerizability of monomers and of their relative stabilities.

The stabilized compositions of this invention are distinguished by their lack of color.

The compositions of the instant invention may also contain additional inhibitors, such as hydroquinone, the monomethyl ether of hydroquinone, (these often being required by monomer specifications) or catechol, tert-butylated hydroquinones or catechols, other alkylated phenols, nitrosophenols and nitrosophenylhydroxylamines.

The inhibited compositions may also contain metal deactivators and UV absorbers to improve light stability; or stabilizers such as amines to retard acid-catalyzed degradation; or thermal or photoinitiators; and other conventional additives.

The process of the instant invention involves simply dissolving an effective inhibiting amount of the inhibitor in the monomer prior to exposure of the latter to conditions where the premature, undesired free radical initiated polymerization might occur.

When it is desired to subject the inhibited monomer to polymerization, the inhibitor can either be removed or overridden by sufficient polymerization initiator. Removal can be accomplished by distillation, absorption or washing with an acidic solution. It is possible to remove the instant 1-hydroxy derivatives while leaving the phenolic antioxidants in the monomer by use of strong acid ion exchange resins. The polymerization inhibiting action of the instant compounds can be overridden by use of sufficient free radical initiator, actinic light irradiation, electron beam exposure or other polymerization initiating means.

The instant invention also pertains to a process which comprises adding 50 to 10,000 of a mixture of components (i) and (ii) in a weight ratio of from 1:10 to 1000:1 to a continuous fluid feed stream to deactivate the autocatalytic polymerization, in any part of the continuous process equipment, such as reactor, reboiler, distillation column, etc., of any ethylenically unsaturated monomer present in the feed stream, and further adding to said feed stream an additional 10 ppm to 500 ppm of said mixture as a makeup additive to maintain the desired concentration of said mixture in the fluid feed stream being processed.

The following examples are presented for the purpose of illustration only and are not to be construed as limiting the instant invention in any manner whatsoever.

The apparatus used in the following experiments is fabricated from an 80 mm OD and 3 mm thick glass tubing, 14 inches (35.6 cm) high, closed on one end and flared at the other end to fit a resin kettle top. The kettle is equipped with a water condenser and nitrogen inlet tube. Except where noted, the polymer reported in the examples is formed in the vapor phase (refluxing) region on the walls of the apparatus about 3 inches (7.6 cm) above the surface of the liquid monomer.

EXAMPLE 1

To demonstrate the need for a pot stabilizer, an experiment is run without any stabilizing additive in the acrylic acid monomer. A dry resin kettle is weighed and the weight recorded. A 100 ml (105 g) aliquot of arcylic acid is charged into the kettle and flushed with dry nitrogen flowing at 250 ml/min for 15 minutes. The kettle is then immersed in an oil bath containing approximately 6 liters of oil such that the surface of the acrylic acid in the kettle is about 2 inches (5.1 cm) below the level of the oil in the bath. The oil bath is heated to 150° C. and the acrylic acid is refluxed for 70 minutes. After approximately 15 minutes, the monomer begins to gel and white insoluble polymer is observed to grow in the monomer liquid. Only a small amount of acrylic acid monomer remains after 70 minutes. The kettle is removed from the oil bath and wiped free of oil. The resulting white polymer is rinsed with hexane to remove residual monomer, dried and weighed to determine the total amount of polymeric material collected inside the kettle. Some 82.9 g of white polymer is obtained. The resin kettle cannot be used for any further experiments.

EXAMPLE 2

To demonstrate the use of a pot stabilizer, 0.105 g (1000 ppm) of a known polymerization inhibitor, phenothiazine, is added to 100 ml (105 g) of acrylic acid and mixed well. The procedure of Example 1 is repeated except that heating is continued for 100 minutes. No polymer is observed in the liquid. The total amount of polymer collected on the inside wall of the kettle in the vapor region (about 3 inches, 7.6 cm, above the level of monomer) is 77.6 g. Phenothiazine has low volatility and protects the liquid monomer from polymerization, but is not effective in the vapor phase.

EXAMPLE 3

To demonstrate the use of a second pot stabilizer, 0.105 g (1000 ppm) of bis(1-oxyl-2,2,6,6-tetramethyl-piperidin-4-yl) sebacate is added to 100 ml (105 g) of acrylic acid and the procedure of Example 2 is repeated. In this case, 64.2 g of white polymer is obtained in the vapor phase and no polymer is seen in the liquid phase. This oxyl compound is not effective in the vapor phase.

EXAMPLE 4

In a comparison experiment, 10.5 mg (100 ppm) of the aluminum salt of N-nitroso phenylhydroxylamine, a commerical polymerization inhibitor, is added to 100 ml (105 g) of acrylic acid along with 1000 ppm of phenothiazine. The procedure of Example 2 is then repeated. During the refluxing period, a number of distinct color changes are observed. Some 29.8 g of polymer is obtained.

EXAMPLES 5-30

Following the general procedure of Example 2, 100 ml (105 g) of acrylic refluxed for 70 minutes in the presence of the stabilizers indicated and the amount of polymer obtained is a measure of the relative effectiveness of the stabilizers used. The lesser is the amount of polymer formed, the more effective is the stabilizer used. The results are given in the table below.

| Example | Additive* (100 ppm) | Pot Stabilizer (1000 ppm) | Polymer Obtained (grams) |
|---|---|---|---|
| 5 | A | phenothiazine | 66.1 |
| 6 | B | none | 51.7 |
| 7 | B | phenothiazine | 5.2 |
| 8 | C | none | 92.3 |
| 9 | C | phenothiazine | 22.5 |
| 10 | D | none | 54.6 |
| 11 | D | phenothiazine | 9.0 |
| 12 | E | phenothiazine | 1.6 |
| 13 | F | phenothiazine | 7.2 |
| 14 | G | phenothiazine | 7.2 |
| 15 | H | phenothiazine | 8.8 |
| 16 | I | phenothiazine | 9.0 |
| 17 | J | phenothiazine | 9.1 |

-continued

| Example | Additive* (100 ppm) | Pot Stabilizer (1000 ppm) | Polymer Obtained (grams) |
|---|---|---|---|
| 18 | K | phenothiazine | 12.6 |
| 19 | L | phenothiazine | 16.3 |
| 20 | M | phenothiazine | 18.4 |
| 21 | N | phenothiazine | 23.4 |
| 22 | O | phenothiazine | 29.3 |
| 23 | P | phenothiazine | 32.3 |
| 24 | Q | phenothiazine | 33.1 |
| 25 | R | phenothiazine | 40.5 |
| 26 | S | phenothiazine | 41.7 |
| 27 | T | phenothiazine | 44.1 |
| 28 | U | phenothiazine | 52.4 |
| 29 | V | phenothiazine | 56.5 |
| 30 | W | phenothiazine | 58.3 |

*A is N,N-diethylhydroxylamine.
B is 1-[2-(methoxycarbonyl)ethoxy]-4-benzyloxy-2,2,6,6-tetramethylpiperidine.
C is 1-methoxy-2,2,6,6-tetramethylpiperidin-4-yl benzoate.
D is bis[1-(2-methoxycarbonyl)ethoxy)-2,2,6,6-tetramethylpiperidin-4-yl] phthalate.
E is 1-tert-butoxy-2,2,6,6-tetramethylpiperidin-4-yl benzoate.
F is 4-hydroxy-1-octyloxy-2,2,6,6-tetramethylpiperidine.
G is 1-[2-(methoxycarbonyl)ethoxy]-2,2,6,6-tetramethylpiperidine.
H is 1-methylcyclohexyloxy-2,2,6,6-tetramethylpiperidin-4-yl benzoate.
I is 4-benzyloxy-1-ethoxy-2,2,6,6-tetramethylpiperidine.
J is 1-carbamoyloxy-4-benzyloxy-2,2,6,6-tetramethylpiperidine.
K is 4-hydroxy-1,2,2,6,6-pentamethylpiperidine.
L is 1-butylcarbamoyloxy-4-benzoyloxy-2,2,6,6-tetramethylpiperidine.
M is 1-α-methylbenzyloxy-2,2,6,6-tetramethylpiperidin-4-yl benzoate.
N is 1,4-dimethoxy-2,2,6,6-tetramethylpiperidine.
O is bis[1-(2-(methoxycarbonyl)ethoxy)-2,2,6,6-tetramethylpiperidin-4-yloxy]-p-xylylene.
P is N,N-di-tert-butylhydroxylamine.
Q is 1-hydroxy-2,2,6,6-piperidin-4-yl benzoate.
R is 4-hydroxy-1-methoxy-2,2,6,6-tetramethylpiperidine.
S is 1-methoxy-2,2,6,6-tetramethylpiperidin-4-one.
T is 1-hydroxy-2,2,6,6-tetramethylpiperidin-4-one.
U is 4-hydroxyethoxy-2,2,6,6-tetramethylpiperidine.
V is bis(1-hydroxy-2,2,6,6-tetramethylpiperidin-4-yl) sebacate.
W is bis(1-octyloxy-2,2,6,6-tetramethylpiperidin-4-yl) sebacate.

EXAMPLES 31-33

When using the procedure of Example 12, the acrylic acid is replaced respectively with the monomers shown below, no polymer is formed in the presence of 100 ppm of 1-tert-butoxy-2,2,6,6-tetramethylpiperidin-4-yl benzoate and 1000 ppm of phenothiazine.

| Example | Monomer |
|---|---|
| 31 | methyl methacrylate |
| 32 | 2-hydroxyethyl methacrylate |
| 33 | 2-hydroxyethyl acrylate |

What is claimed is:

1. A monomer composition, stabilized against premature polymerization, which comprises
    (a) acrylic acid, methacrylic acid, crotonic acid, vinyl acetate or an alkyl or hydroxy-substituted alkyl acrylate or methacrylate ester; and
    (b) an effective amount, sufficient to inhibit premature polymerization of component (a), of a combination of
       (i) phenothiazine; and
       (ii) a compound of formula I, XIV or XV

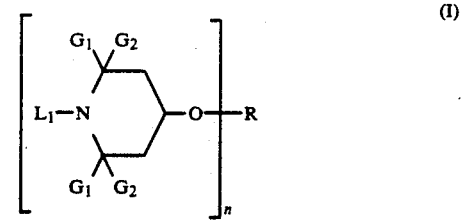

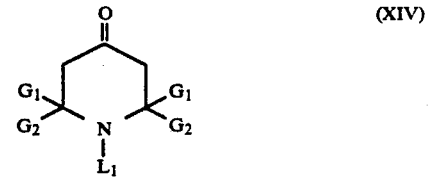

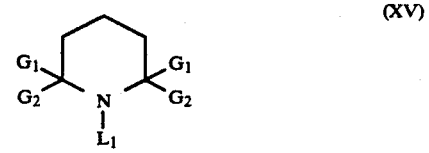

wherein
$G_1$ and $G_2$ are independently alkyl of 1 to 4 carbon atoms;
$L_1$ is hydrogen, alkyl of 1 to 18 carbon atoms, alkyl substituted by cyanoethyl, glycidyl, aralkyl of 7 to 15 carbon atoms or a monovalent acyl radical of an aliphatic, cycloaliphatic, araliphatic or aromatic acid, —OCONHL$_3$ or —OL$_4$, where
$L_3$ is hydrogen, alkyl of 2 to 18 carbon atoms, allyl, cyclohexyl, aryl of 6 to 10 carbon atoms, said aryl substituted by one or two alkyl groups of 1 to 4 carbon atoms or is benzyl,
$L_4$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl of 1 to 4 carbon atoms, or $L_4$ is —CH$_2$CH$_2$COOL$_5$ where $L_5$ is alkyl of 1 to 18 carbon atoms,
n is 1 or 2,
when n is 1,
R is $C_1$–$C_{18}$-alkyl optionally interrupted by one or more oxygen atoms, cyanoethyl, benzyl, glycidyl, a monovalent acyl radical of an aliphatic, cycloaliphatic, araliphatic or aromatic acid, or of carbamic acid or of a phosphorus-containing acid, or a monovalent silyl radical; or
when n is 2,
R is $C_1$–$C_{12}$-alkylene, $C_4$–$C_{12}$-alkenylene, xylylene, a divalent acyl radical of an aliphatic, cycloaliphatic, araliphatic or aromatic dicarboxylic acid, or of a dicarbamic acid or of a phosphorus-containing acid, or a bivalent silyl radical.

2. A composition according to claim 1 wherein (a) is acrylic acid, methacrylic acid, methyl methacrylate, 2-hydroxyethyl methacrylate or 2-hydroxyethyl acrylate.

3. A composition according to claim 1 wherein (a) is acrylic acid; (i) is phenothiazine; and (ii) is a compound of formula I.

4. A composition according to claim 3 wherein (ii) is 1-[2-(methoxycarbonyl)ethoxy]-4-benzyloxy-2,2,6,6-tetramethylpiperidine;
1-methoxy-2,2,6,6-tetramethylpiperidin-4-yl benzoate; or
bis[1-(2-(methoxycarbonyl)ethoxy)-2,2,6,6-tetramethylpiperidin-4-yl] phthalate.

* * * * *